(12) United States Patent
Mercandelli

(10) Patent No.: US 12,036,357 B2
(45) Date of Patent: Jul. 16, 2024

(54) INHALER DEVICE

(71) Applicant: PHARMADEVICES S.R.L., Bologna (IT)

(72) Inventor: Alberto Mercandelli, Bologna (IT)

(73) Assignee: Pharmadevices S.R.L., Bologna (IT)

( * ) Notice: Subject to any disclaimer, the term of this patent is extended or adjusted under 35 U.S.C. 154(b) by 765 days.

(21) Appl. No.: 17/053,445

(22) PCT Filed: May 9, 2018

(86) PCT No.: PCT/IT2018/000066
§ 371 (c)(1),
(2) Date: Nov. 6, 2020

(87) PCT Pub. No.: WO2019/215767
PCT Pub. Date: Nov. 14, 2019

(65) Prior Publication Data
US 2021/0316090 A1   Oct. 14, 2021

(51) Int. Cl.
*A61M 15/00*   (2006.01)
*A61M 11/00*   (2006.01)

(52) U.S. Cl.
CPC .... *A61M 15/0043* (2014.02); *A61M 15/0003* (2014.02); *A61M 15/0023* (2014.02);
(Continued)

(58) Field of Classification Search
CPC .......... A61M 15/0043; A61M 15/0003; A61M 15/0023; A61M 15/0026;
(Continued)

(56) References Cited

U.S. PATENT DOCUMENTS 4,210,140 A * 7/1980 James ............... A61M 15/0028
604/59
4,446,862 A * 5/1984 Baum ............... A61M 15/0043
128/203.15
(Continued)

FOREIGN PATENT DOCUMENTS

EP    0028162 A1   5/1981
EP    0581473 A1   2/1994
(Continued)

OTHER PUBLICATIONS

English translation for WO 2012004518, translated by SEARCH Clarivate Analytics, translated on Aug. 25, 2023.*
(Continued)

*Primary Examiner* — Tu A Vo
(74) *Attorney, Agent, or Firm* — Armstrong Teasdale LLP

(57) ABSTRACT

An inhaler device for delivering a powder substance contained in a capsule includes a main body having a first body portion and a second body portion jointly defining a first capsule seat part adapted to retain a first capsule part. The first and second body portions are hinged to each other so as to be rotatable between a closed main body position, adapted to retain the first capsule part in the first capsule seat part, and an open main body position adapted to allow expulsion of the first capsule part from the first capsule seat part. A slider, formed by a first slide portion and a second slide portion jointly defining a second capsule seat part adapted to retain a second capsule part, is slidingly housed in the main body.

17 Claims, 13 Drawing Sheets

(52) U.S. Cl.
CPC .... *A61M 15/0026* (2014.02); *A61M 15/0031* (2014.02); *A61M 11/003* (2014.02); *A61M 2202/064* (2013.01)

(58) Field of Classification Search
CPC .......... A61M 2202/064; A61M 11/003; A61M 15/003; A61M 15/0031; A61M 15/0028
See application file for complete search history.

(56) References Cited

U.S. PATENT DOCUMENTS

| | | | | |
|---|---|---|---|---|
| 4,860,740 | A | * | 8/1989 | Kirk ................. A61M 15/0031 128/203.15 |
| 2013/0269695 | A1 | | 10/2013 | Brouet et al. |
| 2015/0283338 | A1 | * | 10/2015 | Colosio ............. A61M 15/0028 128/203.15 |

FOREIGN PATENT DOCUMENTS

| | | | |
|---|---|---|---|
| FR | 2968566 A1 | 6/2012 | |
| JP | 2006280676 A | 10/2006 | |
| WO | 8201470 A1 | 5/1982 | |
| WO | 2009091780 A2 | 7/2009 | |
| WO | WO-2012004518 A1 * | 1/2012 | ........ A61M 15/0021 |
| WO | 2014054059 A1 | 4/2014 | |
| WO | WO-2016083102 A1 * | 6/2016 | ............ A61M 13/00 |

OTHER PUBLICATIONS

International Search Report for International Patent Application No. PCT/IT2018/000066, mailed Dec. 19, 2018, 4 pages.

\* cited by examiner

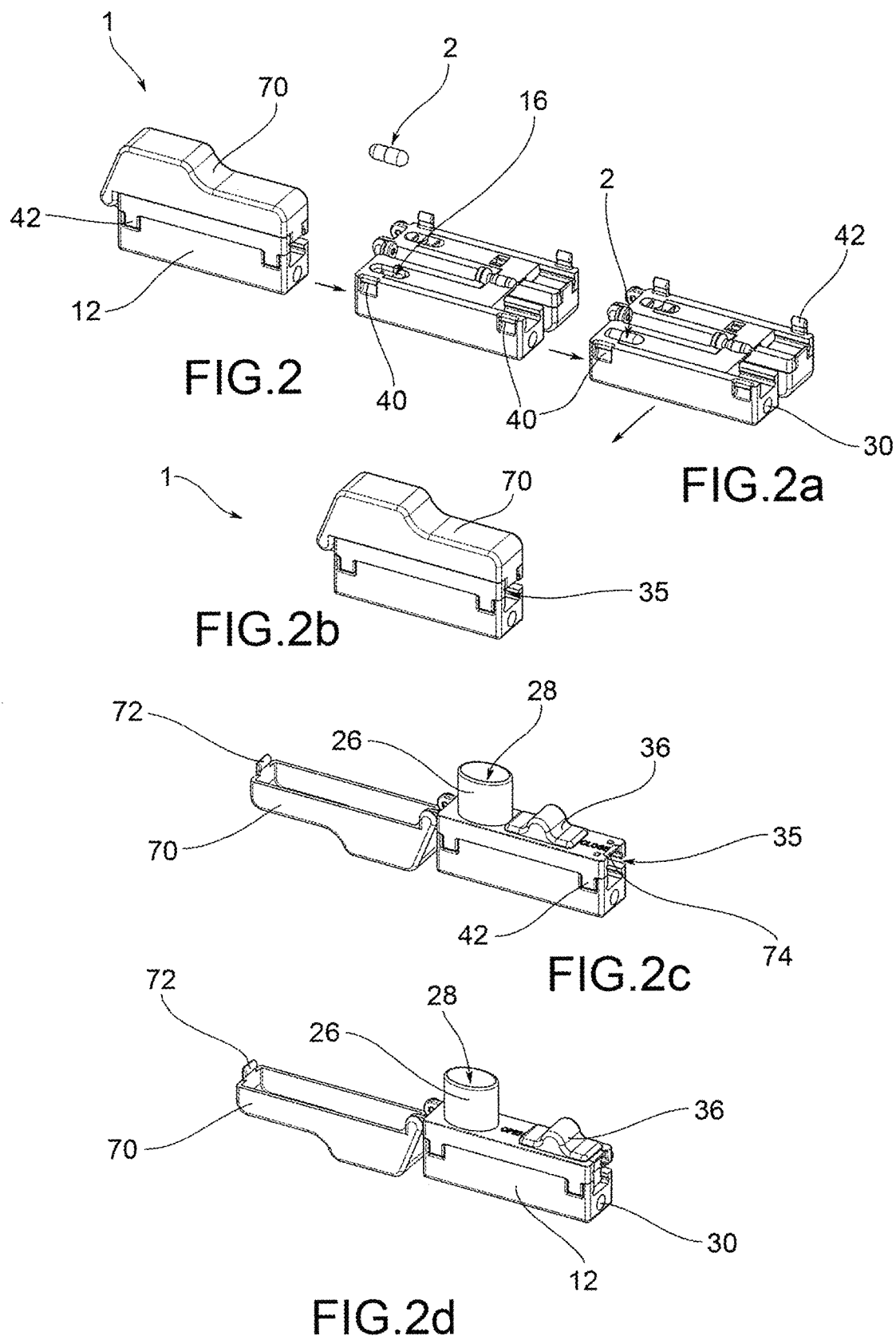

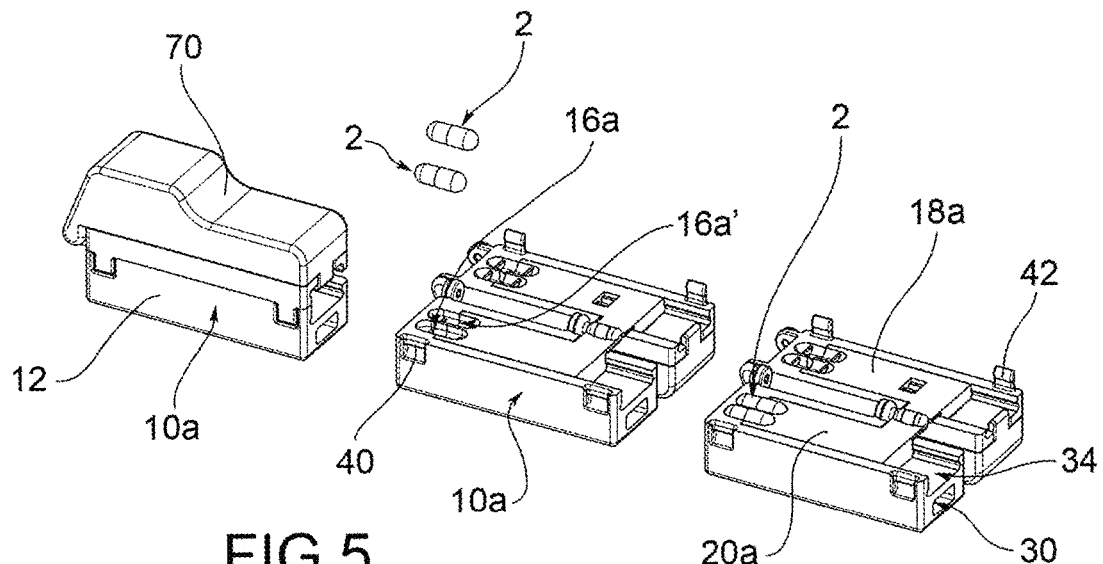
FIG.5
FIG.5a
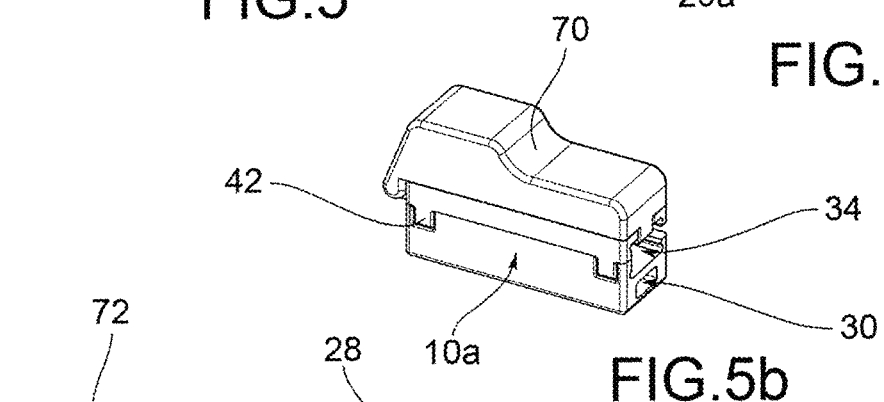
FIG.5b
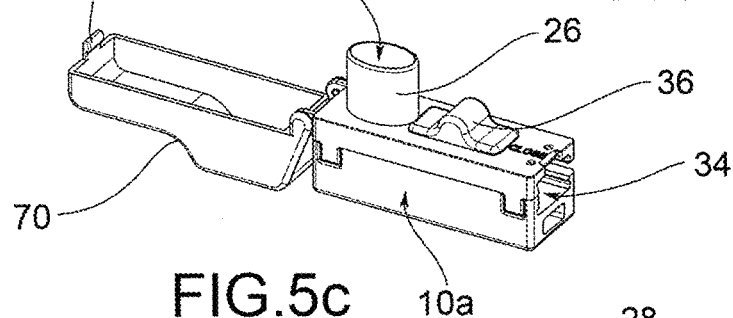
FIG.5c
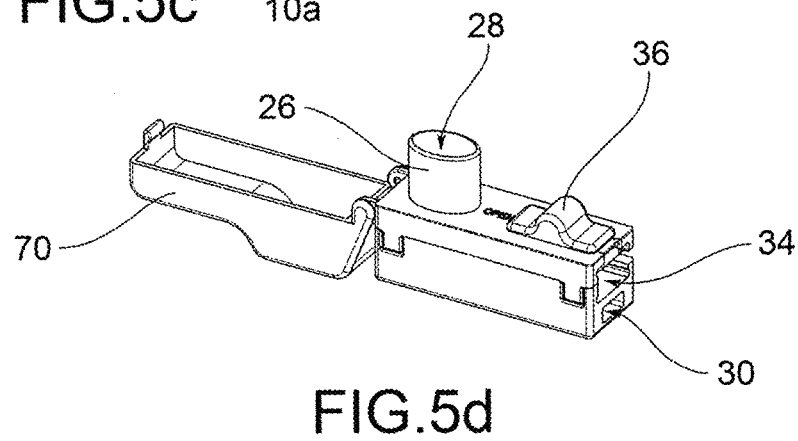
FIG.5d

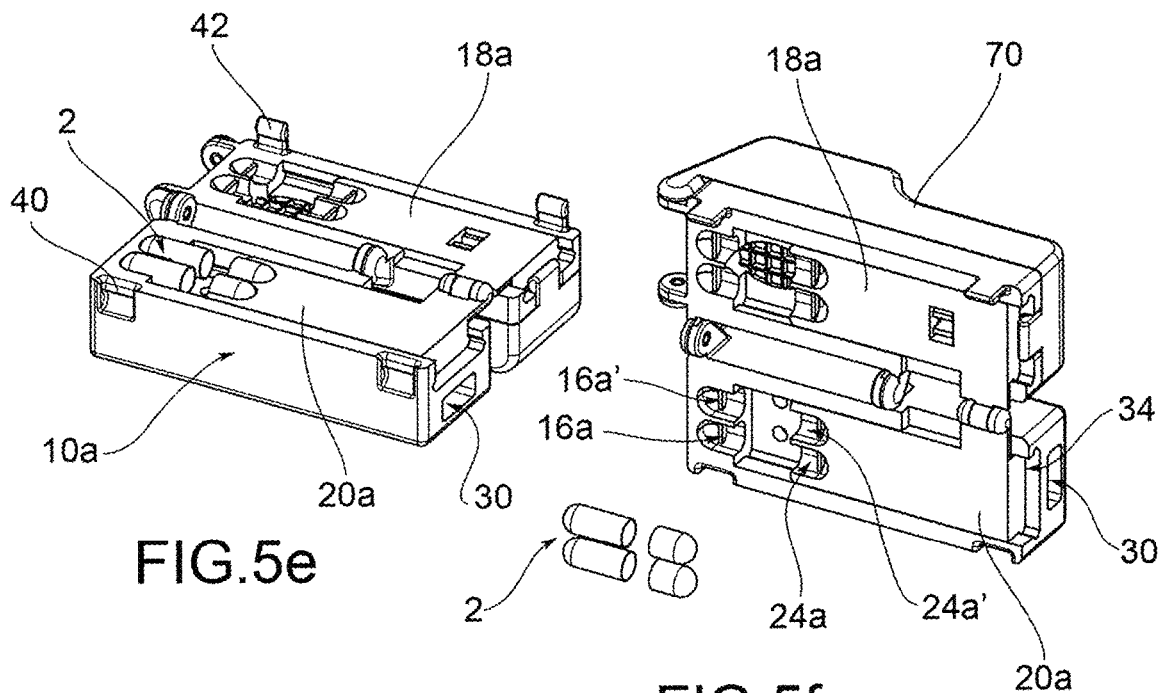
FIG.5e
FIG.5f
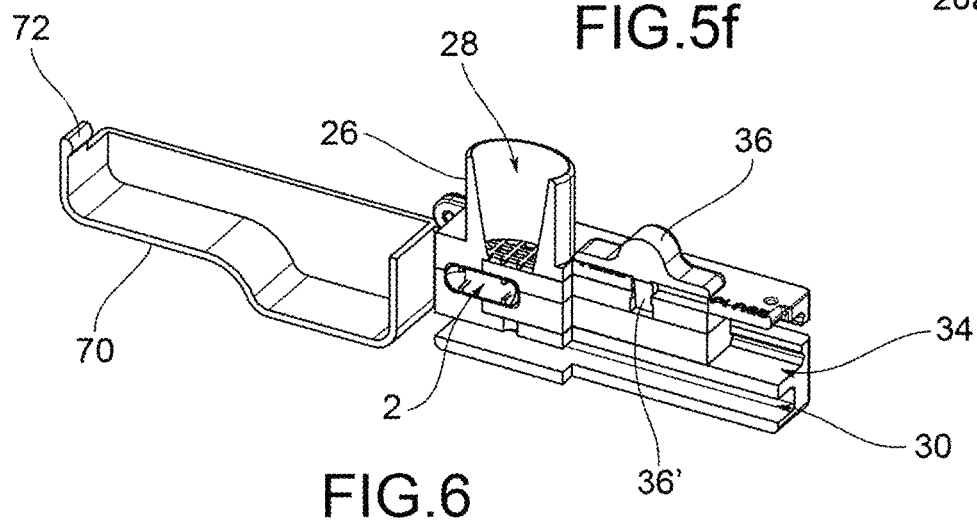
FIG.6
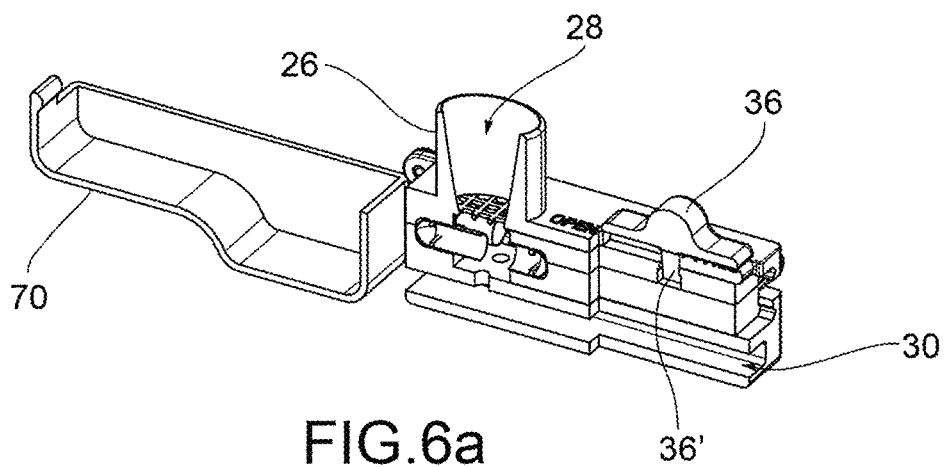
FIG.6a

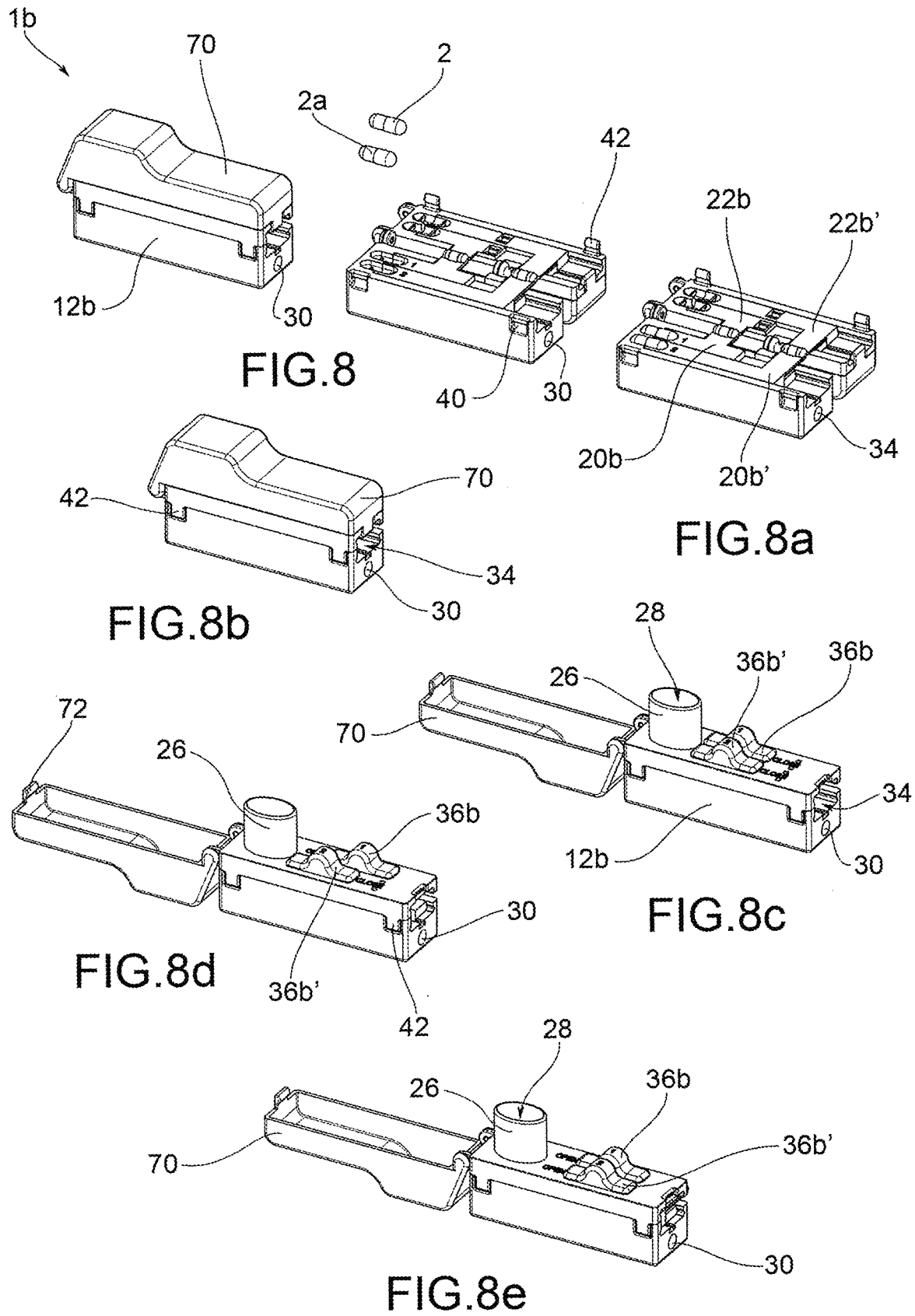

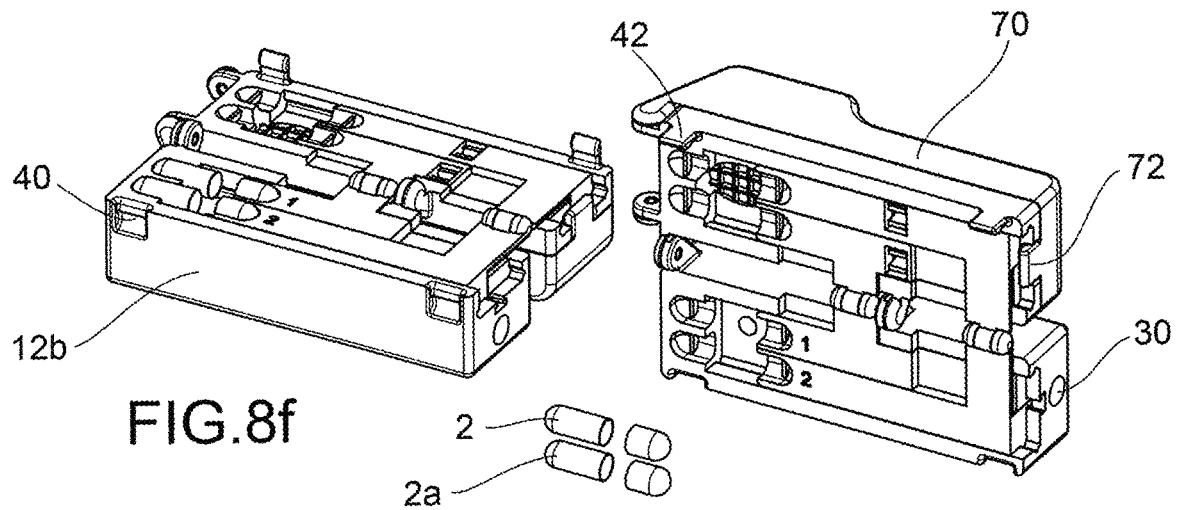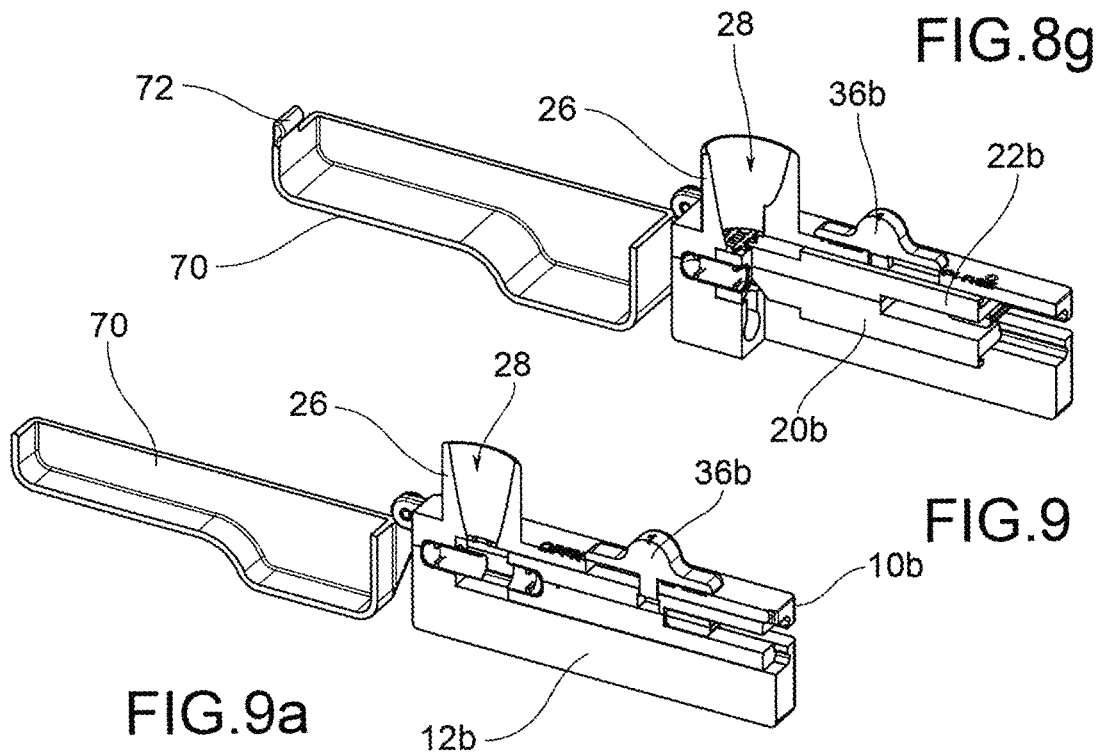

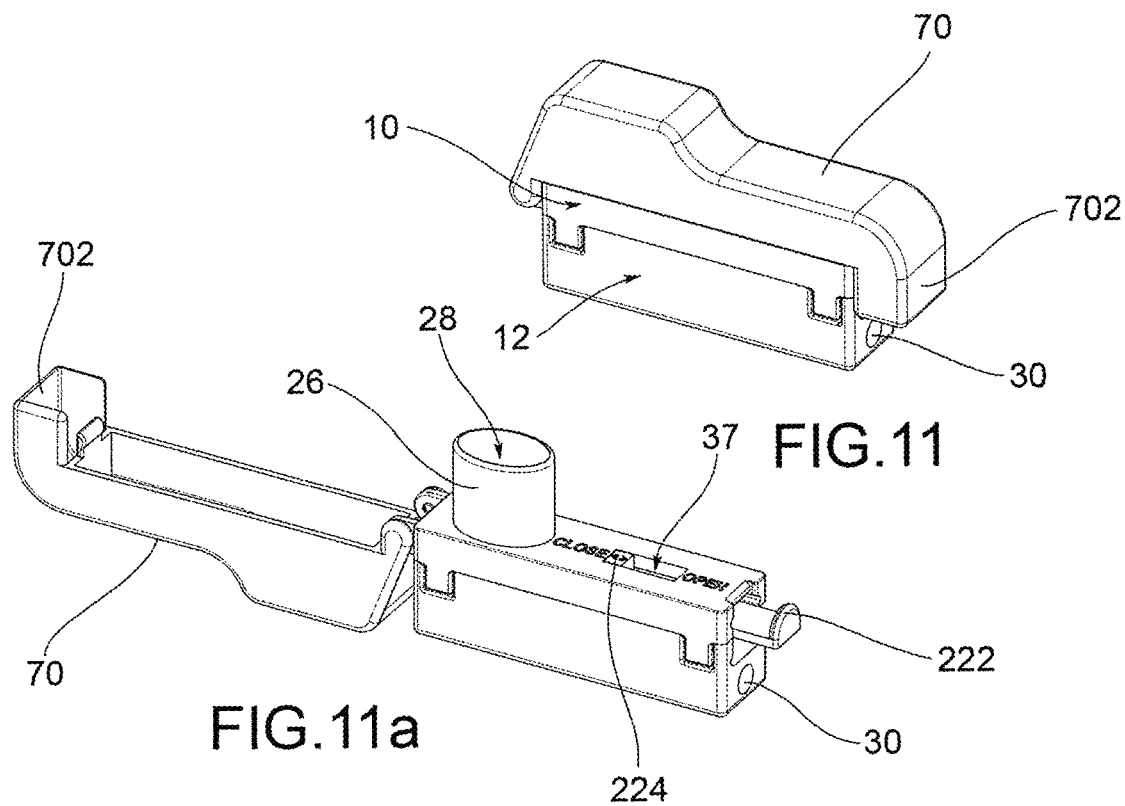
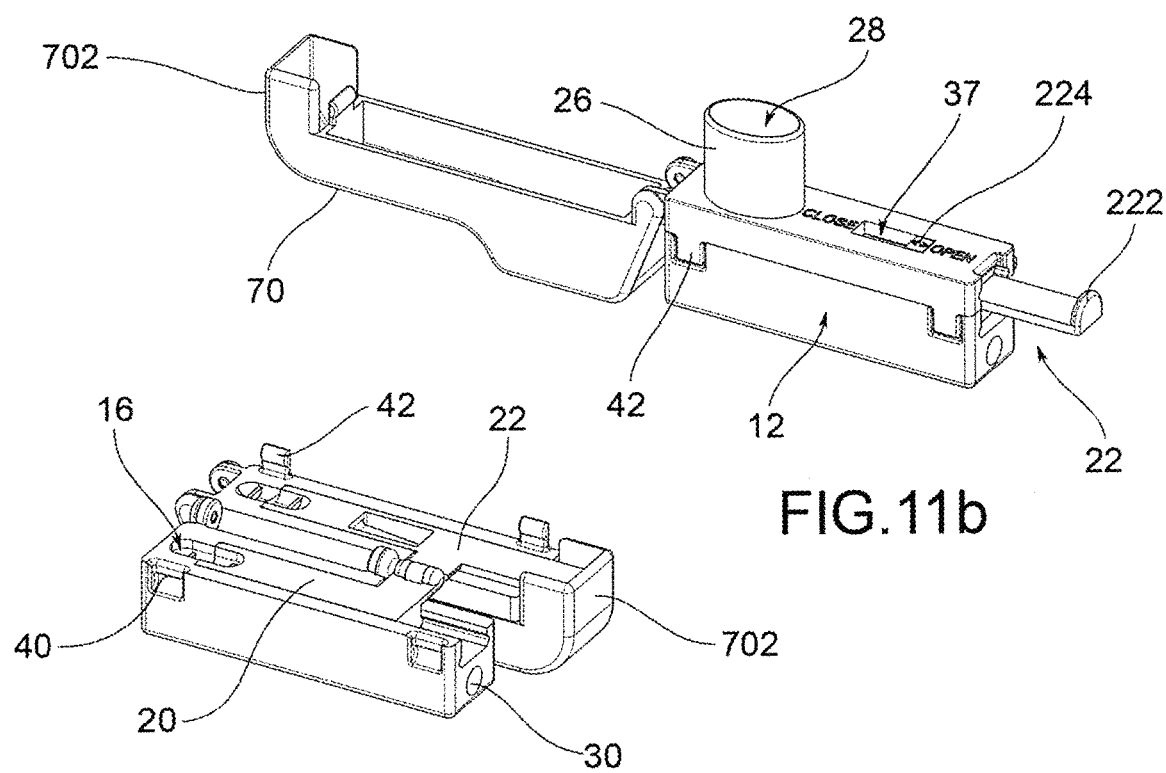

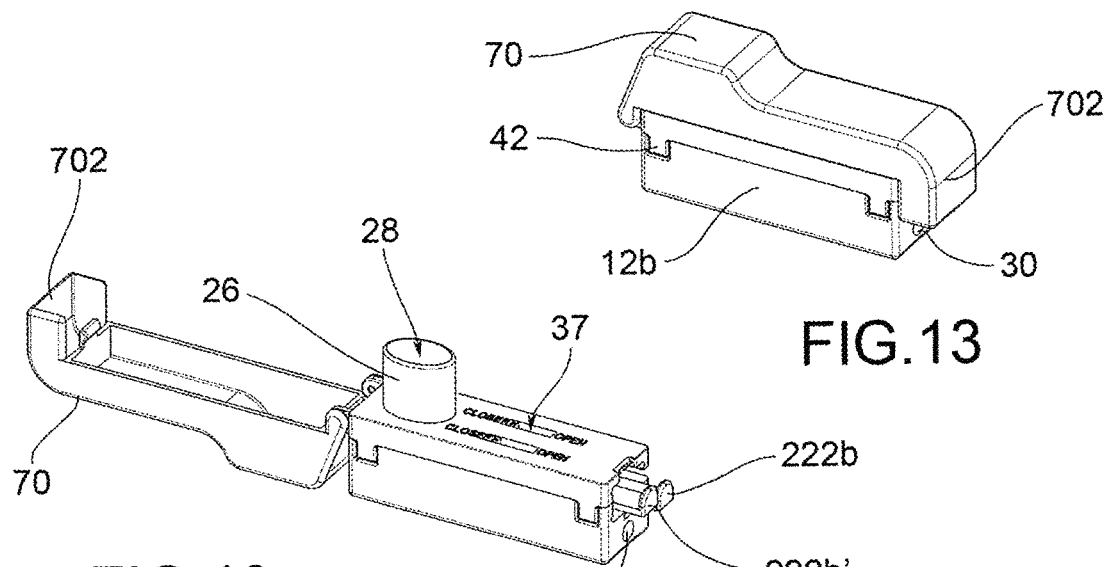
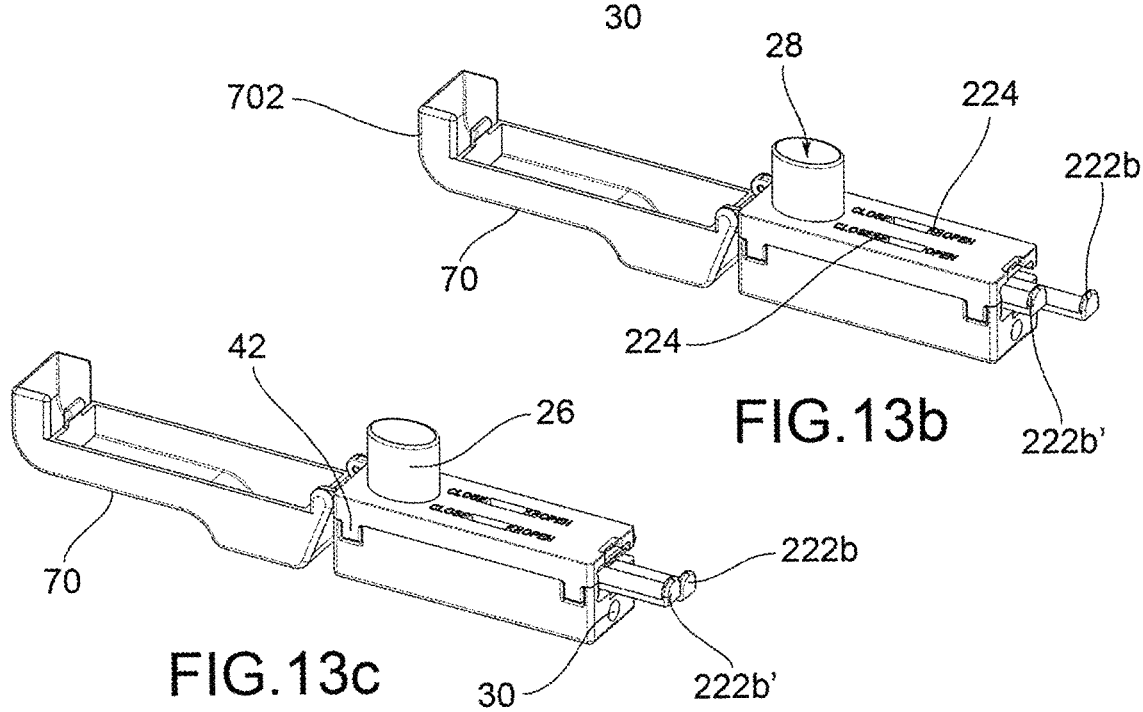
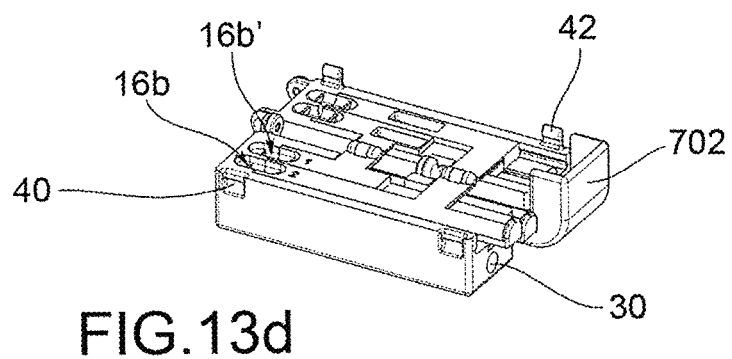
FIG.13
FIG.13a
FIG.13b
FIG.13c
FIG.13d

INHALER DEVICE

CROSS-REFERENCE TO RELATED APPLICATIONS

This application is a National Stage Application of International Patent Application No. PCT/IT2018/000066, having an International Filing Date of May 9, 2018, the entire contents of which are hereby incorporated by reference herein.

FIELD OF THE INVENTION

The present invention relates to an inhaler device adapted for the release to the respiratory tract of a patient of a powdered substance contained in a capsule having a closed container, also called an operculum, formed of two separable parts. For example, said capsule can have any colour, size and dimension according to the pharmaceutical classification used for inhalation applications.

The product contained in the capsule is actually made up of a single chemical unit or several chemical units, one or more of which can be both active pharmaceutical ingredients with recognized pharmaceutical activity and excipients. In particular, for example, the formulation of the substance contained in the capsule can consist either of micronized material (active or excipient) or of non-micronized material. By micronized we mean a product with an average aerodynamic dimension of less than 20 microns (preferably between 0 and 5 microns); by non-micronized we mean a product above 20 microns, preferably between 20 microns and 200 microns.

BACKGROUND OF THE INVENTION

Inhaler devices of this type are already known, comprising a mouthpiece and a body in which a seat suitable for receiving a capsule containing the powder substance to be inhaled is obtained. Said body is associated with means for opening the capsule which can be operated by the user, or automatic means necessary for the purpose of allowing passage through the capsule or operculum of a flow of air coming from the outside which, by mixing with the powdered substance, allows the latter to be extracted from the operculum and redirected towards the mouthpiece of the device and thus towards the patient-user.

In an embodiment illustrated in a patent application WO2014054059A1, the capsule is opened by removing the two capsule parts inside the inhaler device so as to allow inhalation of the powder substance contained in the capsule. This technical solution is particularly advantageous in that it allows avoiding the perforation, cutting or breaking of one or more parts of the capsule to allow the extraction of the powder substance. The inhaler device described in the aforementioned patent application thus allows overcoming the drawback represented by the possible formation of fragments of the operculum which can be mixed with the powdered substance and which can therefore be inhaled by the patient.

The technical solution proposed in WO envisages inserting the capsule into a capsule seat formed by two separate parts, each supported by an elastic arm. Cuneiform separation means associated with the mouthpiece act on said elastic arms causing a diverging thereof and therefore a removal of the two parts of the capsule seat.

Since the bending of the elastic arms in opposite directions makes the two parts of the capsule seat move along a circumferential arc, a sliding friction is generated between the overlapping portions of the two capsule parts which, in some cases, is higher than the friction due to the interference between the walls of the capsule and those of the respective seat. In these cases, the two parts of the capsule do not separate or in any case move relative to the correct position, preventing or hindering an optimal inhalation.

Obviously these situations are very dangerous and unacceptable for a "life-saving" device like the subject one.

Furthermore, when the capsule has been inserted into the capsule seat, the closure of the inhaler device causes the separation of the two capsule seat parts and the user must proceed immediately with inhalation of the substance.

SUMMARY OF THE INVENTION

An object of the present invention is to further improve the reliability and safety of the inhaler device.

Another object of the invention is to propose an inhaler device that also allows housing when closed, one or more capsules immediately ready for use but still intact. In other words, an object of the invention is to provide an inhaler device which also acts as a capsule transport container.

Such objects are achieved by an inhaler device as described and claimed herein.

Advantageous embodiments of the inhaler device are also described.

BRIEF DESCRIPTION OF THE DRAWINGS

The features and the advantages of the inhaler device according to the invention shall be made readily apparent from the following description of preferred embodiments thereof, provided purely by way of a non-limiting example, with reference to the accompanying figures, in which:

FIGS. 2-2f are perspective views of the inhaler device in FIG. 1 in as many operating steps of the device;

FIGS. 5-5f are perspective views of the inhaler device in FIG. 4 in as many operating steps of the device;

FIGS. 6 and 6a are two perspective views in axial section of the inhaler device in the operation steps in FIGS. 5d and 5e, respectively;

FIGS. 8-8g are perspective views of the inhaler device in FIG. 7 in as many operating steps of the device;

FIGS. 9, 9a and 9b are perspective views in axial section of the inhaler device in the operation steps in FIGS. 8c, 8d and 8e, respectively;

FIGS. 11-11c show the inhaler device of FIG. 10 in the closed configuration, in the open configuration for inserting a capsule, in the configuration with the slide in the retracted position and in the configuration with the slide in the advanced position, respectively;

FIGS. 13-13*d* show the device in FIG. 12 in as many operating steps.

DETAILED DESCRIPTION

Figure 1:
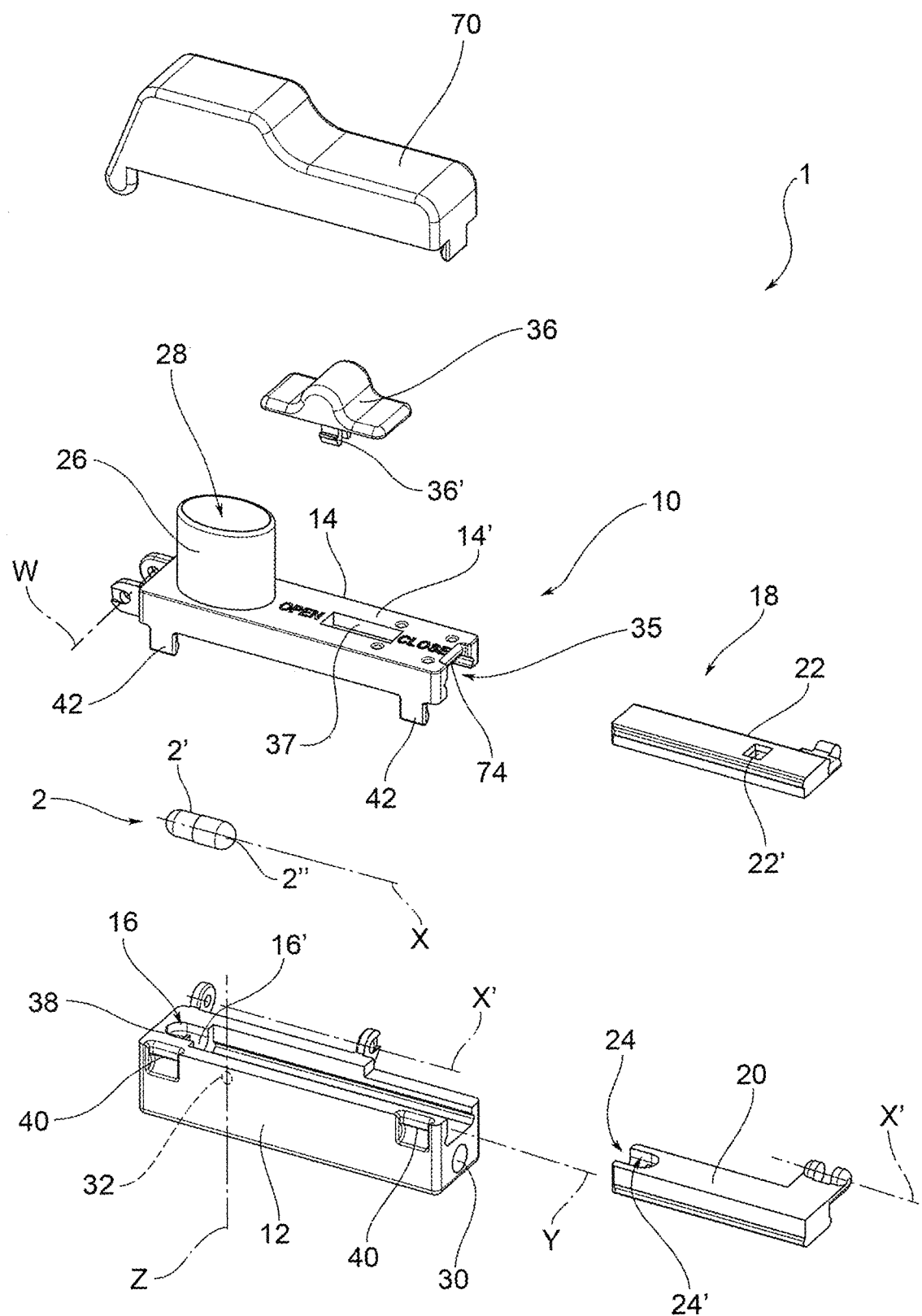
FIG. 1 is an exploded perspective view of the inhaler device according to the invention, in one embodiment.
Figures 2E, 2F:
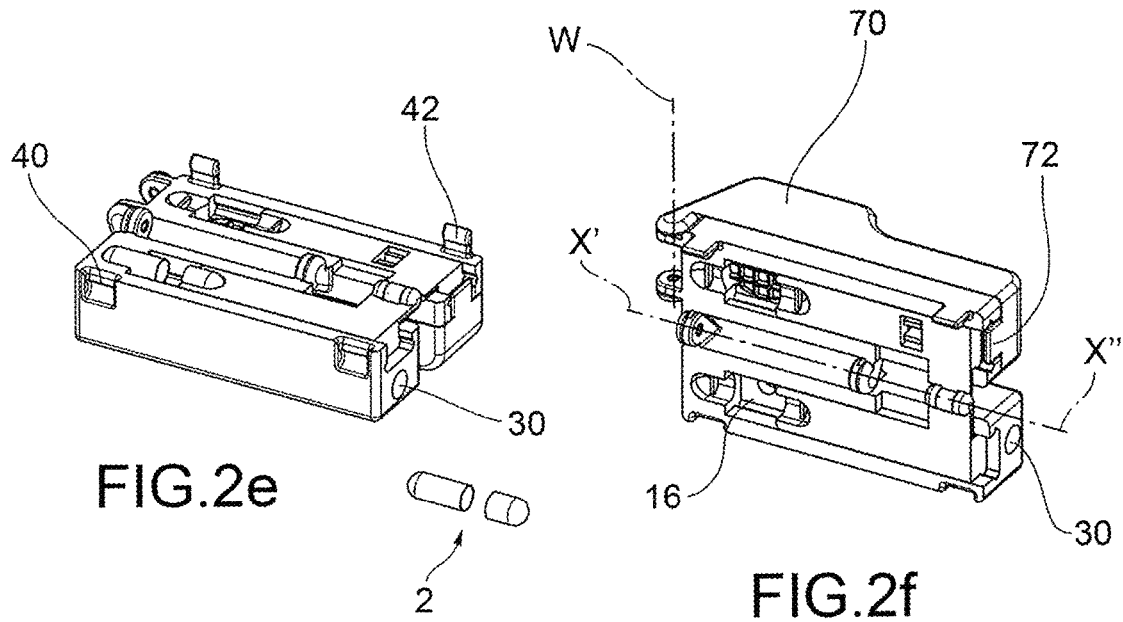
Figure 3:
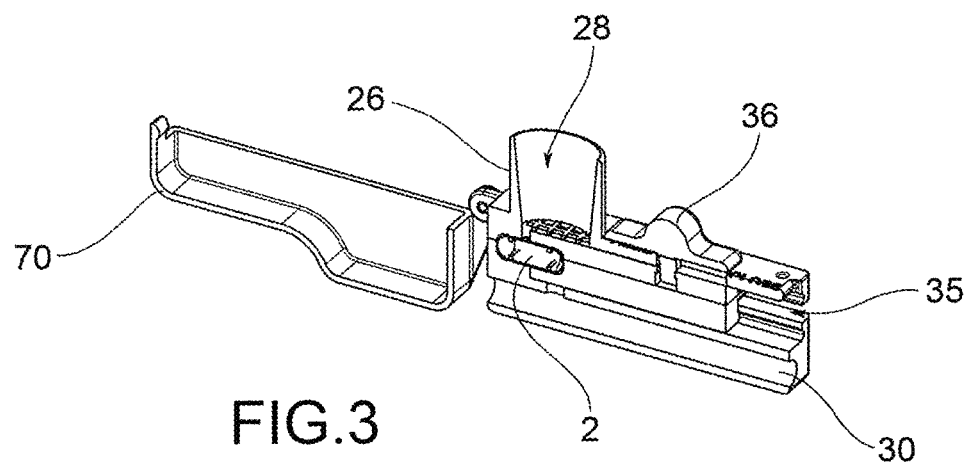
FIGS. 3 and 3a are two perspective views in axial section of the inhaler device in the operation steps in FIGS. 2d and 2e, respectively.
Figure 3A:
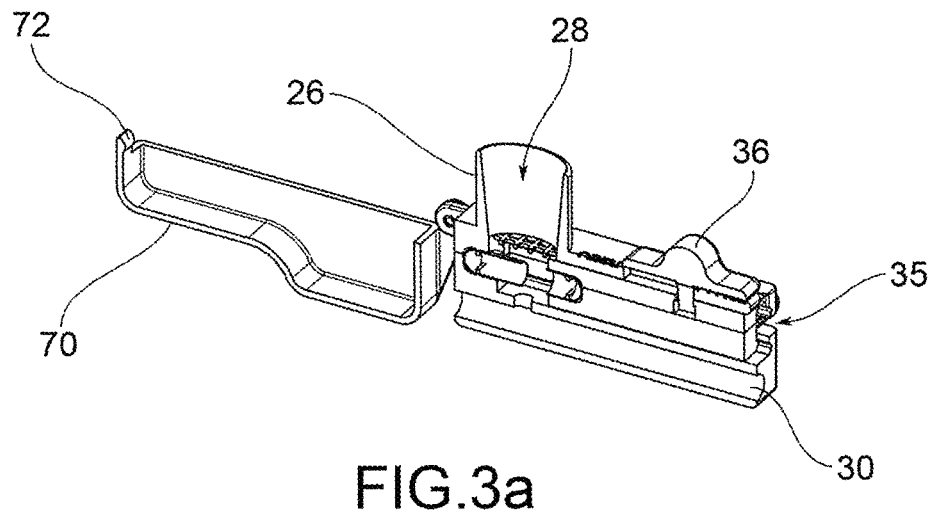
Figure 4:
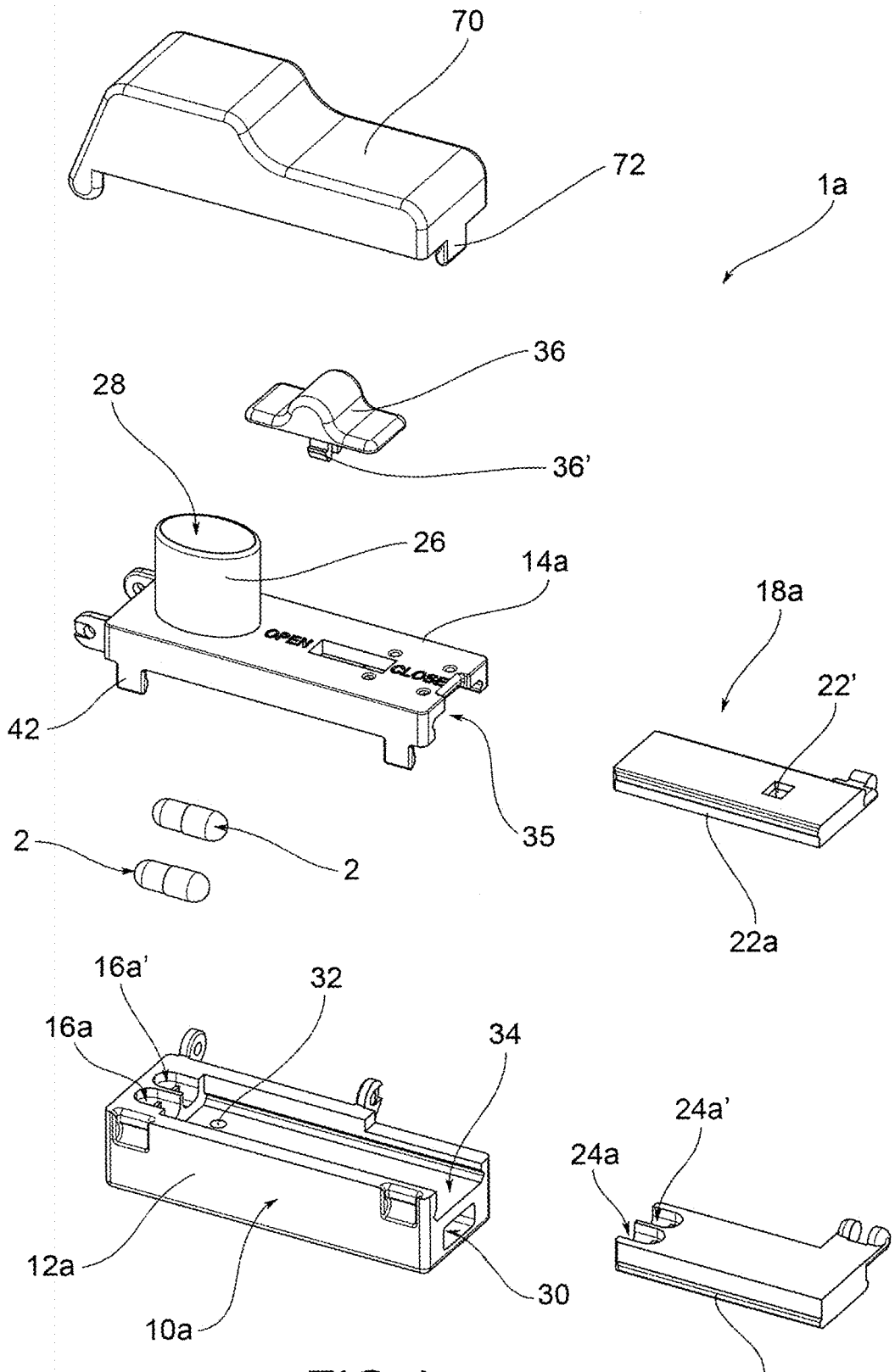
FIG. 4 is an exploded perspective view of the inhaler device according to the invention, in a variant embodiment.
Figure 7:
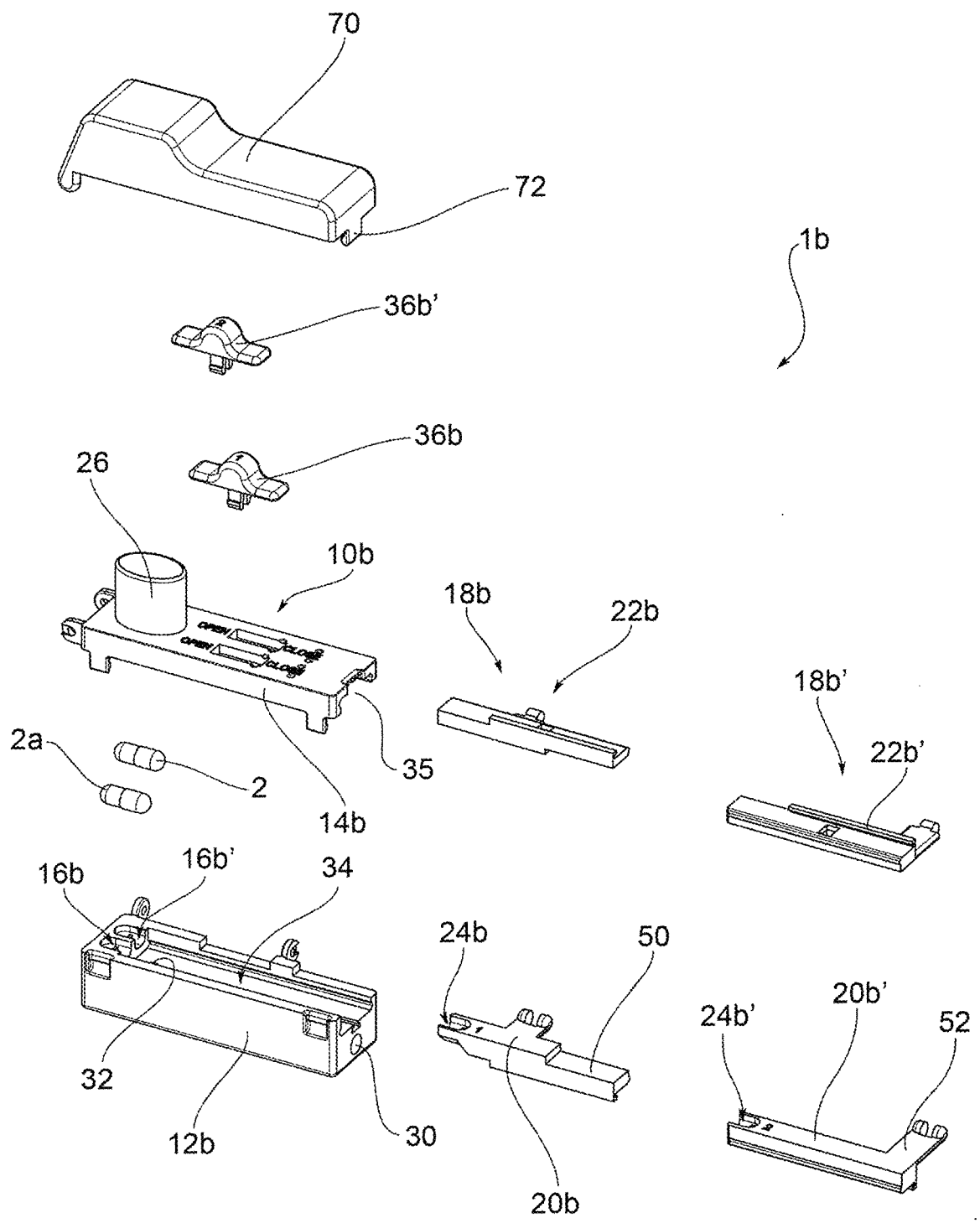
FIG. 7 is an exploded perspective view of the inhaler device according to the invention, in a further embodiment.

With reference to FIGS. 1-3*a*, reference numeral 1 indicates, as a whole and in a first embodiment, an inhaler device of at least one powder substance contained in a capsule 2 of the type having an operculum formed by two parts 2', 2" coupled together along a main capsule axis X.

The inhaler device 1 comprises a main body 10 having a first body portion 12 and a second body portion 14. The two body portions 12, 14 jointly define a first capsule seat part 16 adapted to retain a respective first part 2' of the capsule 2.

The two body portions 12, 14 are hinged to each other so as to be rotatable about a body rotation axis (X') parallel to the main capsule axis (X). The two body portions 12, 14 can be rotated relative to one another between a closed main body position and an open main body position.

In the closed main body position, the two body portions 12, 14 are adapted to retain the first capsule part 2' in the first capsule seat part 16. For example, in this closed main body position, the two body portions 12, 14 are overlapped, or are closed against each other.

In the open main body position, the two body portions 12, 14 are adapted to allow the insertion of the capsule 2 in the inhaler device 1 and, at the end of the inhalation, the expulsion of the first capsule part 2' from the first part of capsule seat 16.

For example, the two body portions 12, 14 can be rotated by about 180°.

The inhaler device 1 further comprises a slide 18 formed by a first slide portion 20 and a second slide portion 22. The two slide portions 20, 22 jointly define a second capsule seat part 24 adapted to retain a respective second capsule part 24. The two slide portions 20, 22 are hinged to each other so as to be rotatable about a slide rotation axis (X") parallel to the main capsule axis (X).

The two slide portions 20, 22 can be rotated between a closed slide position and an open slide position.

In the closed slide position, the two slide portions 20, 22 are adapted to retain the second capsule part 2" in the second capsule seat part 24. For example, in this closed slide position, the two slide portions 20, 22 are overlapped, or are closed against each other.

In the open slide position, the two slide portions 20, 22 are adapted to allow the insertion of the capsule 2 in the inhaler device 1 and, after the inhalation of the substance contained in the capsule, the expulsion of the second capsule part 2" from the second part of capsule seat 24.

The first slide portion 20 is housed in the first body portion 12. The second slide portion 22 is housed in the second body portion 14.

Each slide portion 20, 22 can be moved in and with respect to the respective body portion 12, 14 along a withdrawal axis (Y) parallel to the main capsule axis (X).

In other words, since the two body portions 12, 14 are hinged and therefore integral with each other, and being the two slide portions 20, 22 hinged and therefore integral with each other, the whole slide 18 can be moved in and with respect to the main body 10.

The two slide portion 20, 22 can be moved jointly between an advanced position, in which the first capsule seat part 16 and the second capsule seat part 24 are placed in mutual contact so as to form a capsule seat 4, i.e. a capsule compartment, adapted to receive a capsule 2, and a retracted position, in which the two capsule seat parts 16, 24 are spaced apart to cause separation of the two capsule parts 2', 2".

In one of the two body portions 12, 14, for example in the second body portion 14 which, in the drawings, is the upper body portion, a suction mouthpiece 26 is obtained for the inhalation of the powder substance contained in the capsule 2, mixed with air. The suction mouthpiece 26 defines an outlet duct 28 in fluid communication with the capsule seat 4.

More in detail, the outlet duct 28 opens at a chamber inside the main body formed between the two capsule seat parts 16, 24 when the slide 18 is translated to a retracted position.

In one embodiment, a filter element 29 is associated with the outlet duct which determines the dimensions of the particulate to be inhaled.

It should be noted that, advantageously, the outlet duct 28 terminates as close as possible to the open ends of the two capsule parts 2', 2" when they are separated. In this way, the whole powder substance that comes out of the two capsule parts is introduced into the outlet duct 28.

For mixing with a flow of air drawn from the outside, in one of the two body portions 12, 14 there is provided a suction hole 30 having an inner end 32 open between the two capsule seat parts 16, 24 when they are mutually spaced.

For example, the suction hole 30 is formed in the lower portion 12 of the main body 10.

In one embodiment, the outlet duct 28 and the inner end 32 of the suction hole 30 are formed in respective body portions 12, 14 and, when the device body is closed, are substantially aligned along a suction axis (Z) substantially orthogonal to the withdrawal axis (Y).

In one embodiment, each slide portion 20, 22 is inserted with shape coupling in a respective slide seat 34, 35 formed in the respective body portion 12, 14, so as to be movable exclusively along the withdrawal direction (Y).

For example, the slide portions 20, 22 and the slide seats 34, 35 have a "dovetail" shape.

In one embodiment, one of the two slide portions 20, 22 is integral with a slider 36 sliding along one of the body portions 12, 14. The slider 36 can be operated manually by a user to cause the slide 18 to translate.

For example, the upper portion 22 of the slide 18 is connected to the slider 36, sliding along a flat upper surface 14' of the second body portion 14, through an elongated through opening 37 formed in the second body portion 14.

In one embodiment, the slider 36 is provided with a latching tooth 36' suitable for snapping into a recess 22' formed in the second slide portion 22.

Figure 10:
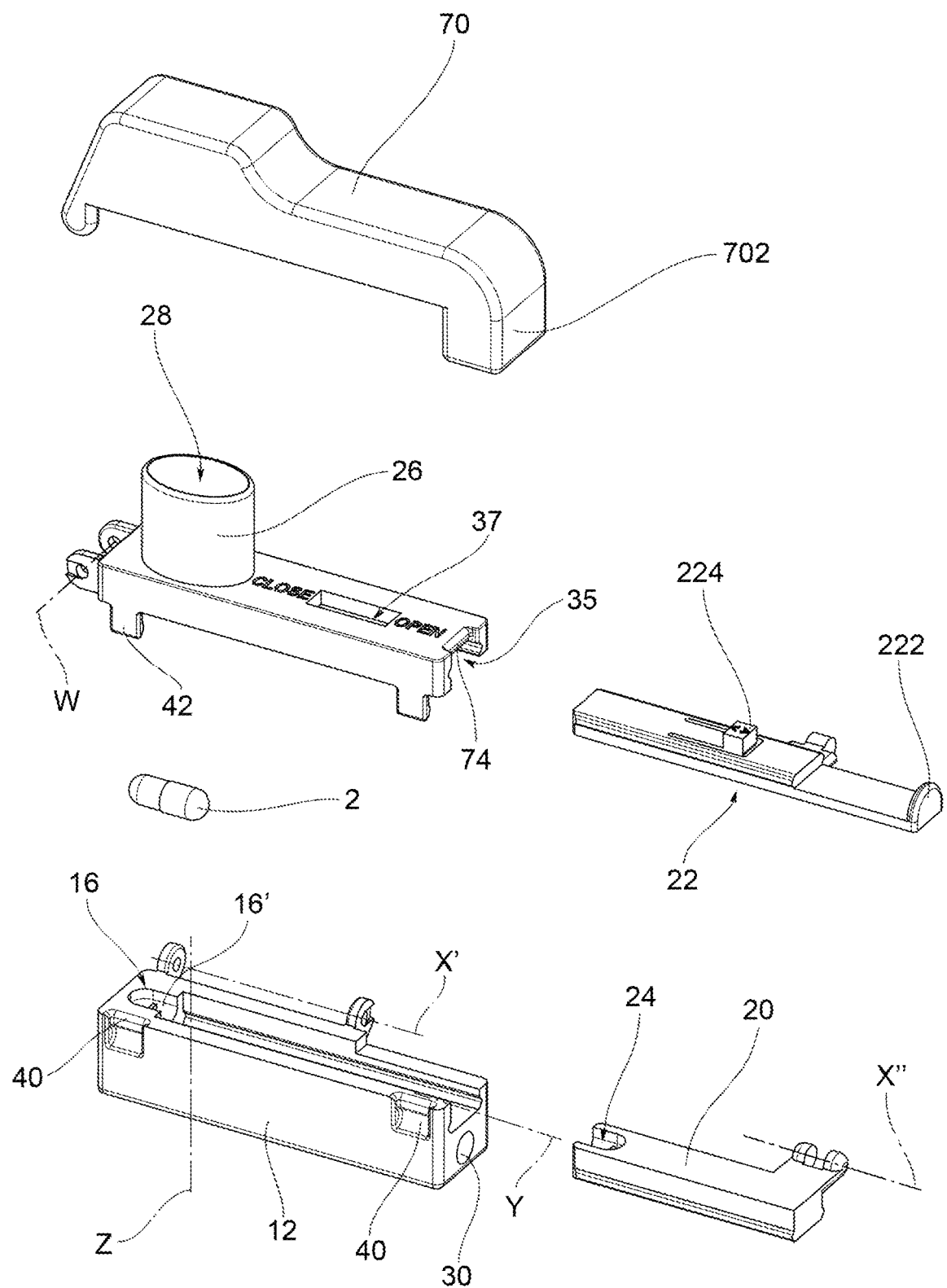
FIG. 10 is an exploded perspective view of the inhaler device according to the invention, in a further embodiment.

In an alternative embodiment illustrated in FIGS. 10 and 11-11*c*, in place of the slider 36, one of the two slide portions 20; 22, for example the upper portion 22, protrudes axially from its seat slide 34; 35 even when it is in an advanced position and ends posteriorly with a gripping element, for example a gripping flange 222, by which the user can operate the slide in translation.

This embodiment therefore makes it possible to avoid making and assembling the slider 36.

In one embodiment, the upper portion 22 of the slide may in any case be provided with an indication projection 224 sliding in the through opening 37 to allow the user to view the position of the slide 18 with respect to the main body 10.

However, the slide 18 is rotatably integral with the main body 10, so that the movement of a body portion relative to the other body portion causes a corresponding movement of a slide portion relative to the other slide portion.

Therefore, it is not necessary to act on the slide portions 20, 22 to cause their rotation towards the opening or closing position of the slide 18, but the two slide portions are driven in rotation by the body portions 12, 14.

In one embodiment, the body rotation axis (X') and the slide rotation axis (X") are coincident, so as to make the device a very compact inhaler and in particular of reduced height. In other words, the elements which form the hinge of the main body 10 are flanked by the elements which form the hinge of the slider 18 in the withdrawal direction (Y).

In an embodiment illustrated in the drawings, the main body 10 has a prevalent extension in the direction of the capsule axis (X). The first capsule seat part 16 is formed near one end of the main body 10. The slide has an extension which is also prevalent in the direction of the capsule axis (X), but such that it remains inside the main body 10 even when it is in a retracted position.

In one embodiment, each body portion 12, 14 and each slide portion 20, 22 substantially forms a half 16', 24' of the respective capsule seat part 16, 24. In other words, while the two capsule seat parts 16, 24 are separated by a separation plane orthogonal to the main capsule axis (X), each capsule seat part 16, 24 is separated by a separation plane parallel to such a main capsule axis (X).

In one embodiment, the two halves 16' of the first capsule seat part 16 and the two slide seats 34, 35 are formed as substantially specular recesses obtained in respective facing surfaces (considering the closed main body) of the two body portions 12, 14.

Similarly, the two halves 24' of the second capsule seat part 24 are formed as substantially mirror-like recesses formed in respective facing surfaces (considering the closed slide) of the two slide portions 20, 22.

In one embodiment, each of the two capsule seat parts 16, 24 is adapted to lock the capsule 2 by interference with the operculum walls.

For example, at least one of the halves of each capsule seat part, preferably in both, at least one locking tooth 38 is provided extending from the bottom of the capsule seat part in a direction substantially orthogonal to the capsule axis X.

In one embodiment, each locking tooth 38 has a decreasing section, for example cuneiform, from the bottom of the capsule seat part so as to facilitate the expulsion of the capsule part at the opening of the main body.

In one embodiment, the two body portions 12, 14 are provided with snap coupling means. For example, in the first body portion 12 two undercuts 40 are formed, spaced apart from each other, in which respective latching tabs which extend from the second body portion 14 are engaged.

In one embodiment, the inhaler device 1 is provided with a protective cover 70 adapted to overlap at least the body portion provided with suction mouthpiece 26, for example the second body portion 14 (the upper portion).

In one embodiment, the protective cover 70 is hinged to the main body 10 so as to rotate around a rotation axis cover (W) orthogonal to the body rotation axis (X'). The protection cover 70 can be provided, on the opposite side with respect to the hinge, with a latching tooth 72 for a snap-on engagement in an undercut 74 formed in the corresponding end of the main body 10.

It should be noted that in the embodiment shown in FIGS. 10 and 11-11c, the protective cover 70 ends with a box-like end portion 702 adapted to enclose and thus 15, protect the end of the slide portion protruding from the main body 10.

FIGS. 4, 5-5f and 6, 6a show the inhaler device 1a in a variant embodiment which allows the containment, the simultaneous opening and therefore the inhalation of two or more capsules 2.

This embodiment differs from the previous one only in that the main body 10a and a single slide 18a form at least two capsule seats 16a, 16a'; 24, 24a' side by side. In this case, the outlet duct 28, at least at the end facing the capsule seats, is positioned in such a way as to have a passage section adapted to receive the powder substances contained in both the capsules.

In a further embodiment shown in FIGS. 7, 8-8g and 9-9b, the inhaler device 1b allows not only the containment of several capsules 2, 2a at the same time, but also their opening and therefore their inhalation in an independent manner, or even at different times.

In fact, in this case, the main body 10b forms at least two capsule seat parts 16b, 16b' side by side and houses at least two slides 18b, 18b' sliding independently from one another.

It should be noted that a respective slider 36b, 36b' is connected to each slide 18b, 18b'.

Figure 12:
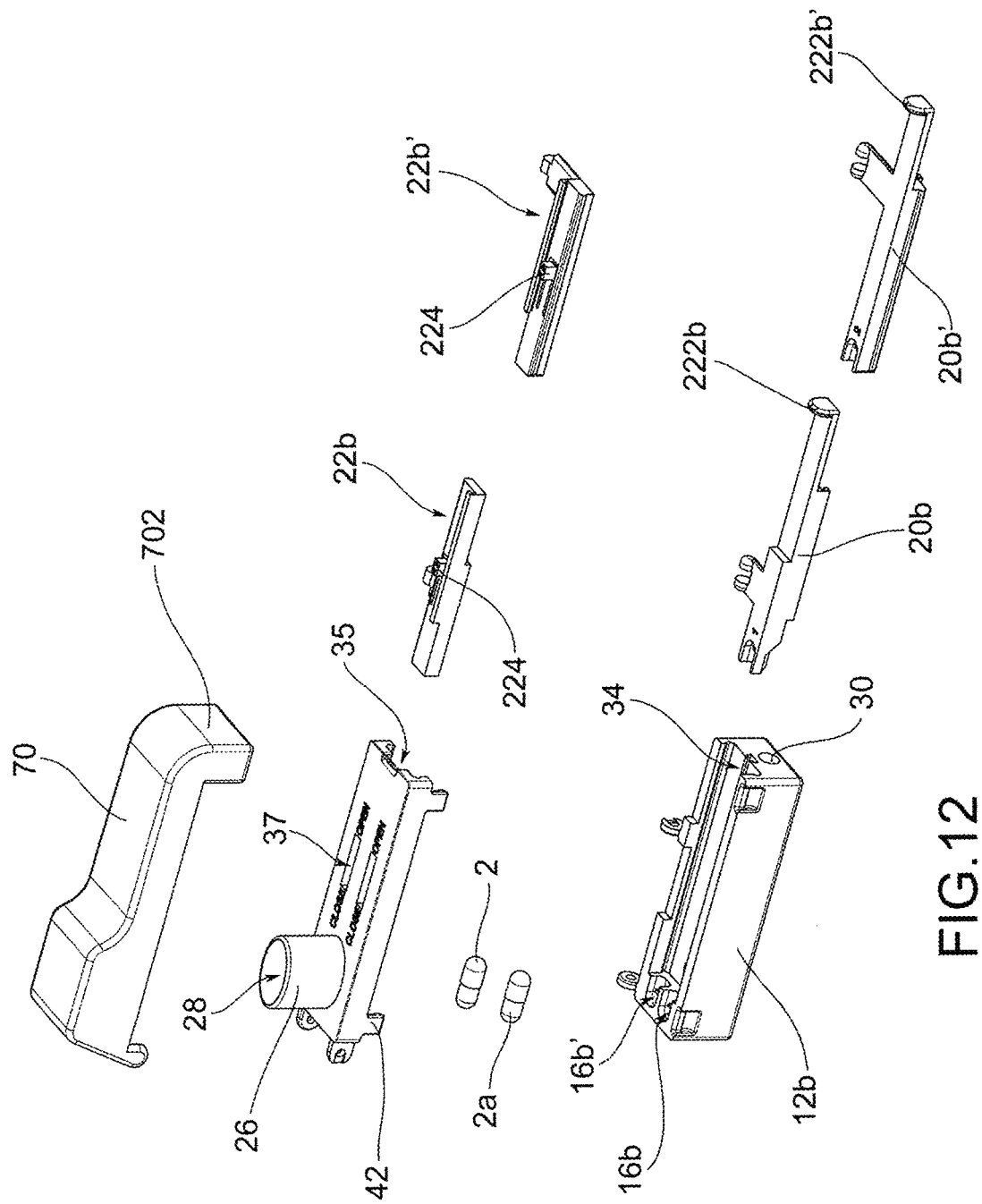
FIG. 12 is an exploded perspective view of the inhaler device according to the invention, in a further embodiment.

As in the case of the device with a single slide, in the embodiment illustrated in FIGS. 12 and 13, instead of the sliders 36b, 36b', each of the two slides has a portion that projects rearwardly from the respective seat and ends with the gripping element 222b, 222b'.

Moreover, in one embodiment, in order to prevent the movement of a slide 18b from interfering with the other slide 18b' and to contain the overall dimensions in length and height of the device, a first slide 18b has the hinge elements positioned between the hinge elements of the main body 10b and a distal portion, i.e. facing the opposite side with respect to the capsule seat part 24b, which forms a slot 50 between the two slide portions 20b, 22b. The second slide 18b' has the hinge elements axially external with respect to the hinge elements of the main body. Moreover, the hinge elements of the second slide 18b' extend from a transverse slide arm 52, or that forms an "L" with the axial portion of the slide 18b', which slides inside the slot 50 of the first slide 18b.

The operation of the inhaler device according to the invention will now be described.

Starting from the completely closed device configuration and with the slide or slides in the advanced position, to insert at least one capsule into a respective capsule seat, the main body is first opened by rotating one part of the body with respect to the other. At this point, it is possible to insert at least one capsule in the respective seat. The main body is then closed.

It should be noted that, in this configuration, the inhaler device can receive and retain at least one capsule ready for use, thus acting as a capsule holder container to also carry out at a later time the inhalation of the substance contained in the capsule.

When the user has to carry out the inhalation, the slide or slides (at the same time or at successive times) is translated into the retracted position, thus causing the separation of the two capsule parts.

At this point, the user can remove the cover and proceed with inhalation through the mouthpiece.

After inhalation, the user can easily extract the two empty capsule parts due to the shape of the locking tooth, as described above.

A man skilled in the art may make several changes, adjustments, adaptations and replacements of elements with other functionally equivalent ones to the embodiments of the inhaler device according to the invention in order to meet incidental needs, without departing from the scope of the following claims. Each of the features described as belonging to a possible embodiment can be obtained independently of the other embodiments described.

What is claimed is:

1. An inhaler device for delivering a powder substance contained in a capsule having an operculum formed by two capsule parts coupled together along a main capsule axis (X), the inhaler device comprising:
   a main body having a first body portion and a second body portion, said first body portion and second body portion defining jointly a first capsule seat part adapted to retain a respective first capsule part of the two capsule parts, the first body portion and the second body portion being hinged to each other so as to be rotatable about a body rotation axis (X') parallel to the main capsule axis (X) between a closed main body position, wherein said first body portion and second body portion are adapted to retain said first capsule part in the first capsule seat part, and an open main body position adapted to allow expulsion of said first capsule part from the first capsule seat part;
   at least one slide formed by a first slide portion and a second slide portion, said first slide portion and second slide portion jointly defining a second capsule seat part adapted to retain a respective second capsule part of the two capsule parts, the first slide portion and the second slide portion being hinged to each other so as to be rotatable about a slide rotation axis (X") parallel to the main capsule axis (X) between a closed slide position, wherein said first slide portion and second slide portion are adapted to retain said second capsule part in the second capsule seat part, and an open slide position adapted to allow expulsion of said second capsule part from the second capsule seat part;
   wherein said first slide portion is housed in said first body portion, said second slide portion is housed in said second body portion, and wherein each slide portion is translatable along a withdrawal axis (Y) parallel to said main capsule axis (X) between an advanced position, in which the first and the second capsule seat parts are placed in mutual contact to form a capsule seat for receiving the capsule, and a retracted position, in which the first and second capsule seat parts are spaced so as to cause separation of said first and second capsule parts.

2. The inhaler device of claim 1, wherein at least one of said first or second body portions comprises a suction mouthpiece of the powder substance contained in the capsule, said suction mouthpiece having an outlet duct in fluid communication with the capsule seat.

3. The inhaler device of claim 2, wherein at least one of said first or second body portions comprises one suction hole having an inner end open between the first and second capsule seat parts when the first and second capsule seat parts are mutually spaced.

4. The inhaler device of claim 3, wherein the outlet duct of the suction mouthpiece is formed in the first body portion and the inner end of the suction hole is formed in the second body portion and, when the main body is closed, the outlet duct of the suction mouthpiece and the inner end of the suction hole are aligned along a suction axis (Z) substantially orthogonal to the withdrawal axis (Y).

5. The inhaler device of claim 1, wherein each slide portion of the first and second slide portions is inserted with shape coupling in a respective slide seat formed in a respective body portion of the first and second body portions, so as to be movable exclusively along the withdrawal axis (Y).

6. The inhaler device of claim 1, wherein at least one of the first or second slide portions is integral with a slider sliding along one of the body portions, said slider configured to be manually operated by a user to cause translation of the at least one slide.

7. The inhaler device of claim 1, wherein at least one of the first or second slide portions, also in the advanced position, protrudes axially from the main body and ends with a gripping element that is grippable by the user to cause translation of the at least one slide.

8. The inhaler device of claim 1, wherein the at least one slide is integral in rotation with the main body, movement of one of the first or second body portion relative to the other of the first or second body portion causing a corresponding movement of one of the first or second slide portion relative to the other of the first or second slide portion, respectively.

9. The inhaler device of claim 1, wherein the body rotation axis (X') and the slide rotation axis (X") coincide.

10. The inhaler device of claim 1, wherein the main body has a prevalent extension in direction of the main capsule axis (X), in which the first capsule seat part is obtained near one end of the main body, and wherein the at least one slide has an extension in direction of the main capsule axis (X) such that the at least one slide remains inside the main body also in the retracted position.

11. The inhaler device of claim 1, wherein each portion of the first and second body portions and each portion of the first and second slide portions of the at least one slide form one half of the respective capsule seat part of the first and second capsule seat parts.

12. The inhaler device of claim 11, wherein at least one of the halves of each capsule seat part of the first and second capsule seat parts comprises at least one locking tooth extending from the bottom of each capsule seat part of the first and second capsule seat parts in a direction substantially orthogonal to the main capsule axis (X).

13. The inhaler device of claim 12, wherein said at least one locking tooth has a section decreasing from the bottom of each capsule seat part of the first and second capsule seat parts to facilitate the expulsion of the respective capsule part of the two capsule parts at an opening of the main body.

14. The inhaler device of claim 1, wherein each capsule seat part of the first and second capsule seat parts is adapted to block the capsule by interference with operculum walls of the capsule.

15. The inhaler device of claim 1, wherein the main body and a single slide form at least two capsule seats side by side.

16. The inhaler device of claim 1, wherein the main body forms the first capsule seat part and a third capsule seat part side by side, the third capsule seat part is configured to receive a second capsule, and wherein the at least one slide and a second slide are housed in the main body, the at least one slide and the second slide are configured to slide independently of each other to allow inhalation of substances contained, respectively, in the capsule and in the second capsule at different times.

17. The inhaler device of claim 1, wherein the first and second body portions are provided with snap coupling means.

* * * * *